(12) United States Patent
Arbouzov

(10) Patent No.: US 11,317,813 B2
(45) Date of Patent: May 3, 2022

(54) MULTI-SENSOR, MODULAR, SUBJECT OBSERVATION AND MONITORING SYSTEM

(71) Applicant: Ivan Arbouzov, Mansfield, TX (US)

(72) Inventor: Ivan Arbouzov, Mansfield, TX (US)

(*) Notice: Subject to any disclaimer, the term of this patent is extended or adjusted under 35 U.S.C. 154(b) by 0 days.

(21) Appl. No.: 15/565,635

(22) PCT Filed: Apr. 11, 2016

(86) PCT No.: PCT/US2016/026945
§ 371 (c)(1),
(2) Date: Oct. 10, 2017

(87) PCT Pub. No.: WO2016/164904
PCT Pub. Date: Oct. 13, 2016

(65) Prior Publication Data
US 2018/0082037 A1  Mar. 22, 2018

Related U.S. Application Data

(60) Provisional application No. 62/145,942, filed on Apr. 10, 2015.

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/0022* (2013.01); *A61B 5/0077* (2013.01);
(Continued)

(58) Field of Classification Search
CPC .... A61B 2560/0223; A61B 2560/0238; A61B 2560/0242; A61B 2560/0252;
(Continued)

(56) References Cited

U.S. PATENT DOCUMENTS

| 5,689,241 A | 11/1997 | Clarke et al. |
| 6,011,477 A | 1/2000 | Teodorescu et al. |

(Continued)

FOREIGN PATENT DOCUMENTS

| CN | 101972140 | 1/2011 |
| CN | 103169453 | 6/2013 |

(Continued)

OTHER PUBLICATIONS

International Search Report and Written Opinion issued in International Application No. PCT/US2016/026945, dated Jul. 6, 2016, 10 pages.

(Continued)

*Primary Examiner* — Jonathan T Kuo
*Assistant Examiner* — Vynm V Huh
(74) *Attorney, Agent, or Firm* — Fish & Richardson P.C.

(57) ABSTRACT

An observation unit (OU) and auxiliary observation unit (AOU) sensor are calibrated in relation to an ambient environment. The OU sensor and the AOU sensor are calibrated in relation to an observational subject. Monitoring parameters are established for the calibrated sensors using a receiving unit (RU). Monitoring types are activated using the RU. Data is gathered from the OU sensor and the AOU sensor. A determination is made that the gathered data exceeds the established monitoring parameters. One or more alerts are generated based on the determination.

20 Claims, 6 Drawing Sheets

(51) Int. Cl.
| | |
|---|---|
| *A61B 5/01* | (2006.01) |
| *A61B 5/08* | (2006.01) |
| *A61B 5/11* | (2006.01) |
| *A61B 5/113* | (2006.01) |
| *A61B 7/00* | (2006.01) |
| *G16H 40/40* | (2018.01) |
| *G16H 40/67* | (2018.01) |
| *A61B 5/024* | (2006.01) |
| *A61B 5/087* | (2006.01) |
| *G01J 5/00* | (2006.01) |

(52) U.S. Cl.
CPC .......... *A61B 5/015* (2013.01); *A61B 5/02055* (2013.01); *A61B 5/0816* (2013.01); *A61B 5/1128* (2013.01); *A61B 5/1135* (2013.01); *A61B 5/4011* (2013.01); *A61B 5/4818* (2013.01); *A61B 5/6801* (2013.01); *A61B 5/6892* (2013.01); *A61B 7/003* (2013.01); *G16H 40/40* (2018.01); *G16H 40/67* (2018.01); *A61B 5/02405* (2013.01); *A61B 5/0878* (2013.01); *A61B 5/1116* (2013.01); *A61B 2560/0223* (2013.01); *A61B 2560/0238* (2013.01); *A61B 2560/0242* (2013.01); *A61B 2560/0252* (2013.01); *A61B 2560/0257* (2013.01); *A61B 2562/029* (2013.01); *G01J 2005/0048* (2013.01); *G01J 2005/0081* (2013.01)

(58) Field of Classification Search
CPC ...... A61B 2560/0257; A61B 2562/029; A61B 5/0022; A61B 5/0077; A61B 5/015; A61B 5/0205; A61B 5/02055; A61B 5/02405; A61B 5/0816; A61B 5/0878; A61B 5/1116; A61B 5/1128; A61B 5/1135; A61B 5/4011; A61B 5/4818; A61B 5/6801; A61B 5/6892; A61B 7/003; A61B 1/042; A61B 1/05; G01J 2005/0048; G01J 2005/0081; G06F 19/3418; G16H 40/40; A45F 2200/0533; A63F 2009/2435; A63F 2300/1087

USPC .................................................. 600/300–301
See application file for complete search history.

(56) References Cited

U.S. PATENT DOCUMENTS

| | | | |
|---|---|---|---|
| 7,928,393 B2 | 4/2011 | Brady et al. | |
| 2005/0245839 A1* | 11/2005 | Stivoric | G06F 19/3418 600/549 |
| 2007/0153871 A1* | 7/2007 | Fraden | A61B 5/015 374/121 |
| 2011/0112442 A1 | 5/2011 | Merger et al. | |
| 2011/0169911 A1* | 7/2011 | Gabura | G06T 11/001 348/32 |
| 2012/0157796 A1 | 6/2012 | Ten Eyck et al. | |
| 2013/0192071 A1 | 8/2013 | Esposito et al. | |
| 2014/0005502 A1* | 1/2014 | Klap | A61B 5/113 600/301 |
| 2014/0232516 A1 | 8/2014 | Stivoric | |
| 2015/0094544 A1* | 4/2015 | Spolin | A61B 5/7275 600/301 |

FOREIGN PATENT DOCUMENTS

| | | |
|---|---|---|
| WO | WO2006060746 | 6/2006 |
| WO | WO2009138976 | 11/2009 |
| WO | WO2014060938 | 4/2014 |

OTHER PUBLICATIONS

European Extended Search Report issued in EP16777488.4, dated Sep. 20, 2018 (8 pages.
Office Action issued in CN201680032160.1, dated Dec. 1, 2020 (15 pages).
Office Action issued in Chinese Patent Application No. 201680032160, dated Apr. 1, 2021 (11 pages).
European Office Action received in EP 16 777 488.4, dated Apr. 28, 2021 (6 pages).

\* cited by examiner

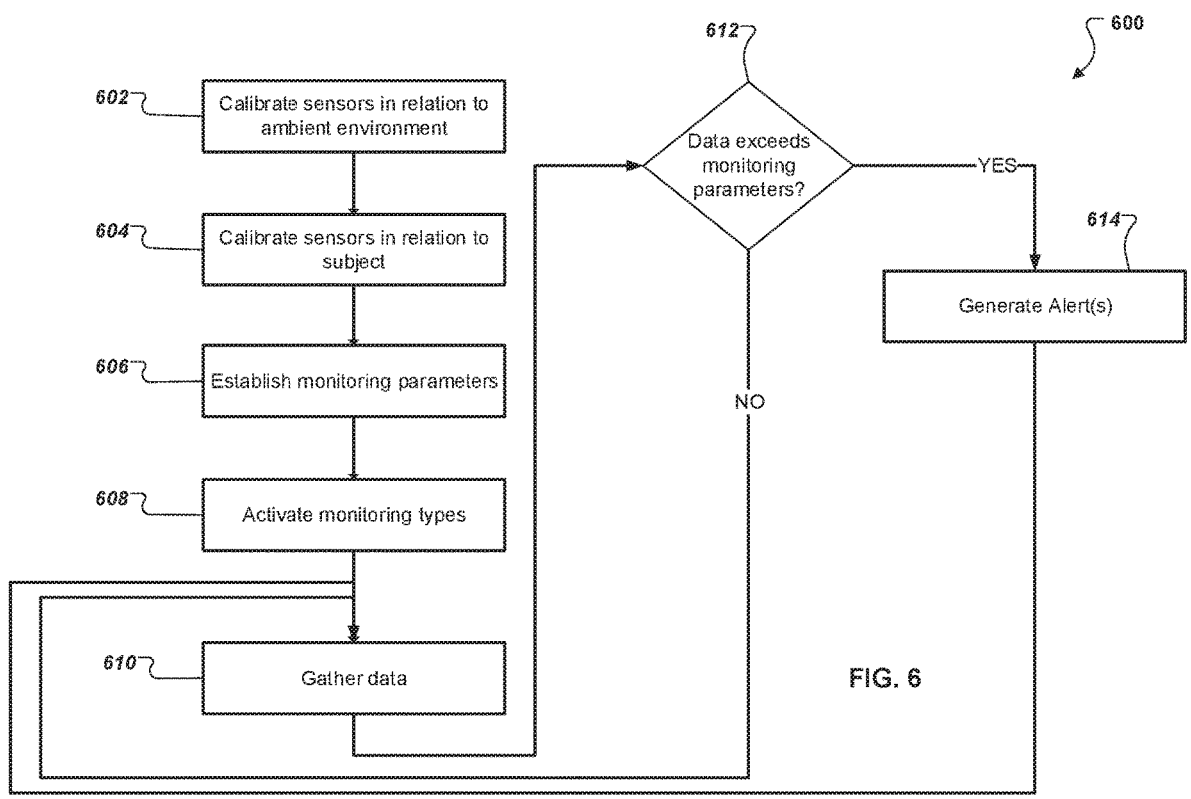

MULTI-SENSOR, MODULAR, SUBJECT OBSERVATION AND MONITORING SYSTEM

CLAIM OF PRIORITY

This application is a National Stage of International Application No. PCT/US2016/026945 filed on Apr. 11, 2016, which claims priority to U.S. Patent Application No. 62/145,942 filed on Apr. 10, 2015, the entire contents of which are hereby incorporated by reference.

BACKGROUND

Currently, observation and monitoring of subjects (for example, babies, children, or medical patients) involves the use of devices designed to primarily obtain and transmit visual and auditory information about a particular subject and for an observer/monitor to make conclusions about the condition/health of the subject based almost exclusively on the received visual and auditory information. For example, traditional baby monitors provide basic audio and/or video information to caregivers (for example, parents, babysitters, daycare workers, nurses, or doctors) which permits a caregiver to evaluate the condition/health of an infant based on whether a child is crying, some aspect of the nature of the child's crying, and/or on some aspect seen in a received visual image. However, in many instances, caregivers may not be skilled at interpreting received audio and/or visual cues for potential health emergency situations or properly assessing the condition/health of a particular subject based on the traditionally received basic audio/visual data. Additionally, the traditionally received basic audio and/or video data fails to provide data necessary to generate specific alerts, useful data (for example, respiratory rate, heart rate, or core body temperature), and/or additional data (for example, logs or charts) that can, in some situations, enhance caregiver response time to mitigate/eliminate potentially life-threating situations associated with an observed subject (for example, the onset of sudden infant death syndrome (SIDS), irregular breathing, temperature variations, heart arrhythmias, or pulmonary aspiration) or provide useful historical information for medical analysis.

SUMMARY

The present disclosure describes a multi-sensor, modular, observation and monitoring system (MMOS). Other implementations of this aspect can include corresponding computer systems, apparatuses, and computer programs recorded on one or more computer-readable media/storage devices, each configured to perform actions of methods associated with the described multi-sensor, modular, observational system. A system of one or more computers can be configured to perform particular operations or actions by virtue of having software, firmware, hardware, or a combination of software, firmware, or hardware installed on the system, that in operation, causes the system to perform the actions. One or more computer programs can be configured to perform particular operations or actions by virtue of including instructions that, when executed by data processing apparatus, cause the apparatus to perform the actions.

In an implementation, an observation unit (OU) and auxiliary observation unit (AOU) sensor are calibrated in relation to an ambient environment. The OU sensor and the AOU sensor are calibrated in relation to an observational subject. Monitoring parameters are established for the calibrated sensors using a receiving unit (RU). Monitoring types are activated using the RU. Data is gathered from the OU sensor and the AOU sensor. A determination is made that the gathered data exceeds the established monitoring parameters. One or more alerts are generated based on the determination.

The subject matter described in this specification can be implemented in particular implementations so as to realize one or more of the following advantages. First, the MMOS provides a caregiver with important additional physical data associated with an observed subject. The additional physical data (for example, respiratory rate, heart rate, or core body temperature) can be useful for the caregiver in making a more comprehensive and holistic evaluation of the condition/health of an observed subject under their care. Second, the additional physical data can be used in combination with traditionally provided audio and/or visual data to enhance response time to mitigate/eliminate potential health emergency situations. Third, the MMOS provides additional, easy-to-use, remote sensors (auxiliary observation units (AOUs)) that can be placed on (for example, directly attached to the body—such as an electrocardiogram sensor), near (for example, attached to a mattress or clothing item), and/or around (for example, in the same room) a monitored subject to provide specifically needed and more precise monitoring data (for example, heart rate, breathing rate, skin temperature, or audio indications of pain/discomfort). Fourth, the MMOS permits preset or dynamic variation of alert parameter thresholds for a multitude of data parameters in order to generate alarms if the alert parameter thresholds are exceeded (for example, skin temperature too low/high, breathing rate too shallow, low/stopped, or high—such as in sleep apnea, or a heart in arrhythmia). If one or more alert parameter thresholds are exceeded, the caregiver can determine whether to make additional inquiries as to the condition/health of the monitored subject or the MMOS can initiate automatic inquiries. Fifth, the MMOS can provide two-way (and/or multiple-way) audio/video communications to reassure a monitored subject, for historical and/or training, and/or for other purposes. Sixth, the MMOS can provide additional features such as voice activation/control, music/voice playback, a night light, an alarm, olfactory stimulation/therapy, initiating operation of heating/cooling equipment, and/or initiating operation of medical or other devices. Seventh, The MMOS can permit the use of third-party sensor units to provide expanded functionality. Eighth, the MMOS can interface with a wide-range of mobile or other computing devices (for example, televisions, smart phones, tablet computers, wearable computers (for example, head-mounted smart device such as GOOGLE GLASS), smart watches, laptop computers) to provide receiving unit (RU) functionality. Receiving unit functionality can include audio/visual or other evaluation of received observation data from one-or-more observation units (OUs)/AOUs, compilation of the received and evaluated observation data, and/or generation of alarms based on alert parameter thresholds. Ninth, the MMOS can provide historical information (for example, logs or charts) useful for medical analysis. Other advantages will be apparent to those of ordinary skill in the art.

The details of one or more implementations of the subject matter of this specification are set forth in the accompanying drawings and the description below. Other features, aspects, and advantages of the subject matter will become apparent from the description, the drawings, and the claims.

DESCRIPTION OF DRAWINGS

FIG. 6 is a flow chart of a method of use of the MMOS according to an implementation.

Like reference numbers and designations in the various drawings indicate like elements.

DETAILED DESCRIPTION

Figure 1:
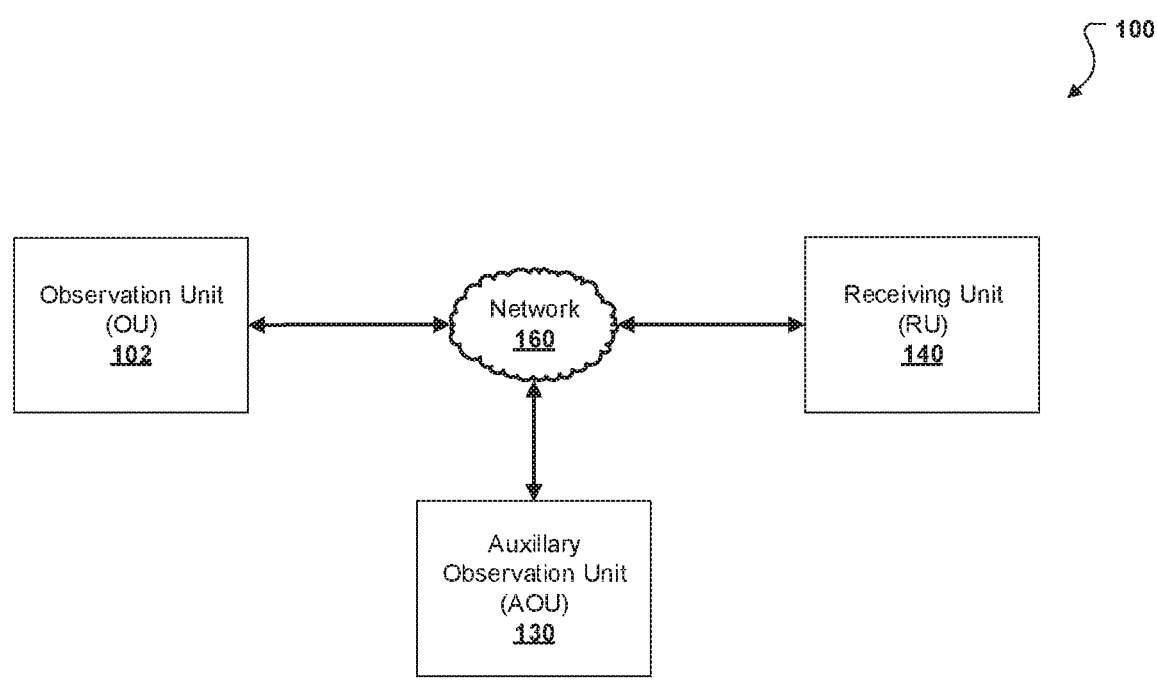
FIG. 1 illustrates a high-level system view of a multi-sensor, modular, observation and monitoring system (MMOS) according to an implementation.

The following detailed description is presented to enable any person skilled in the art to make, use, and/or practice the disclosed subject matter and is provided in the context of one or more particular implementations. Various modifications to the disclosed implementations will be readily apparent to those skilled in the art, and the general principles defined herein may be applied to other implementations and applications without departing from the scope of the disclosure. Thus, the present disclosure is not intended to be limited to the described and/or illustrated implementations but is to be accorded the widest scope consistent with the principles and features disclosed herein.

At a high level, what is described is a multi-sensor, modular, observation and monitoring system (MMOS). Currently, observation and monitoring of subjects (for example, babies, children, or medical patients) involves the use of devices designed to primarily obtain and transmit visual and auditory information about a particular subject and for an observer/monitor to make conclusions about the condition/health of the subject based almost exclusively on the received visual and auditory information. For example, traditional baby monitors provide basic audio and/or video information to caregivers (for example, parents, babysitters, daycare workers, nurses, or doctors) which permits a caregiver to evaluate the condition/health of an infant based on whether a child is crying, some aspect of the nature of the child's crying, and/or on some aspect seen in a received visual image. However, in many instances, caregivers may not be skilled at interpreting received audio and/or visual cues for potential health emergency situations or properly assessing the condition/health of a particular subject based on the traditionally received basic audio/visual data. Additionally, the traditionally received basic audio and/or video data fails to provide data necessary to generate specific alerts, useful data (for example, respiratory rate, heart rate, or core body temperature), and/or additional data (for example, logs or charts) that can, in some situations, enhance caregiver response time to mitigate/eliminate potentially life-threating situations associated with an observed subject (for example, the onset of sudden infant death syndrome (SIDS), irregular breathing, temperature variations, heart arrhythmias, or pulmonary aspiration) or provide useful historical information for medical analysis.

The described MMOS provides a caregiver with important additional physical data associated with an observed subject. For example, the additional physical data (for example, respiratory rate, heart rate, or core body temperature) can be useful to the caregiver in making a more comprehensive and holistic evaluation of the condition/health of an observed subject under their care. The additional physical data can also be used in combination with traditionally provided audio and/or visual data to enhance response time to mitigate/eliminate potential health emergency situations. To obtain the additional physical data, in some implementations, the MMOS provides additional, easy-to-use remote sensors (auxiliary observation units (AOUs)) that can be placed on (for example, directly attached to the body—such as an electrocardiogram sensor), near (for example, attached to a mattress or clothing item), and/or around (for example, in the same room) a monitored subject to provide specifically needed and more precise monitoring data (for example, heart rate, breathing rate, skin temperature, or audio indications of pain/discomfort).

In some implementations, the MMOS permits preset or dynamic variation of alert parameter thresholds for a multitude of alert data parameters in order to generate alarms if the alert parameter thresholds are exceeded (for example, skin temperature too low/high, breathing rate too shallow, low/stopped, or high—such as in sleep apnea, or a heart in arrhythmia). If one or more alert parameter thresholds are exceeded, the caregiver can determine whether to make additional inquiries as to the condition/health of the monitored subject or the MMOS can initiate automatic inquiries. In some implementations, an alert parameter threshold can be dynamically varied based on changes to one or more alert parameter values/changes in on or more alert parameter thresholds.

In some instances, the MMOS can also provide two-way (and/or multiple-way) audio/video communications to reassure a monitored subject that their needs are being addressed (for example, to re-assure a small child, inform a hospital patient that assistance being sent, or a request assistance of a caregiver). In another example, an observer can communicate with a subject while a third-party only monitors and/or records the audio and/or video communication for historical, training, and/or other purposes.

In some implementations, the MMOS can provide additional features such as voice activation/control, music/voice playback (for example, playback of a recording of a parent reading a book to a child), a night light, an alarm (for example, generated audio and/or visual strobe (for example, for emergency situations)), olfactory stimulation/therapy (for example, for Alzheimer's or dementia patients), initiating operation of heating/cooling equipment (for example, heating/cooling pad or air conditioning/heating), and/or initiating operation of medical (for example, breathing therapy systems, oxygen supplementation devices, continuous positive airway pressure (CPAP) machines) or other devices.

The MMOS can also be configured, in some instances, to permit the use of third-party sensor units to provide expanded sensor and analysis functionality; including the ability to interface with a wide-range of mobile or other computing devices (for example, televisions (picture-in-picture and other modes), smart phones, tablet computers, wearable computers (such as head-mounted smart device such as GOOGLE GLASS), smart watches, and/or laptop computers) to provide receiving unit (RU) functionality. RU functionality can include audio/visual or other evaluation of received observation data from one-or-more observation units (OUs)/AOUs (for example, monitored subject temperature, body position, breathing rate, or heart rate), compilation of the received and evaluated observation data, and/or generation of alarms based on alert parameter thresholds. For example, a child lying in different positions or uncovered emits different amounts of thermal energy detectable using a thermal imaging camera and/or thermometer. Image recognition algorithms (for example, analyzing thermal and/or daylight visual images) executing on an OU, AOU, and/or an RU can initiate an alarm and/or other automatic reactions if a visual image cross-checked with a physical wearable thermometer indicates that the child's skin/core body temperature is detected to have dropped below alert parameter thresholds. Ninth, the MMOS can provide historical information (for example, logs or charts) useful for medical analysis.

FIG. 1 illustrates a high-level system view of a multi-sensor, modular, observation and monitoring system (MMOS) 100 according to an implementation. In typical implementations, the MMOS 100 includes an observation unit (OU) 102, optional auxiliary observation unit (AOU) 130, and a receiving unit (RU) 140 communicatively coupled by a network 160. Note that while the MMOS 100 is illustrated in a particular example configuration in FIG. 1, the MMOS 100 is not limited by the illustrated implementation. As will be apparent to those of ordinary skill in the art, there are many possible configurations of the MMOS 100 consistent with this disclosure and the following descriptions. Other configurations consistent with this disclosure are considered to be within the scope of this disclosure. For example, in other implementations, the MMOS 100 can contain more or fewer components and/or the communicative coupling can be provided by more than one network. In typical implementations, the network 160 can be one or more of a WIFI, BLUETOOTH, cellular, and/or other transmission means consistent with this disclosure.

In typical operation, temperature measurements (for example, from a thermal camera, digital thermometer, etc.) are gathered by components of the MMOS 100 and used to determine health, comfort, position, etc. of an observed/monitored subject by using an amount of heat transmitted by the subject (for example, skin, breath, etc.) and recognition mapping of, for example, exposed skin, areas of exposed skin (for example, determine subject position, skin temperature, etc.), breath temperature (for example, breathing regularity, core body temperature, position of subject, etc.), and the like. One or more software applications can be used to calculate position mapping and temperature of subject (for example, a baby) in a field-of-view of a camera. Other applications can be used to calibrate the various components of the MMOS 100. For example, one or more applications can allow a camera to be positioned and calibrated for a particular subject, calibrated for normal skin/breath temperature, calibrated for various body positions, calibrate ambient audio, temperature, humidity, or olfactory condition, etc. in a room, and the like. Olfactory condition could indicate the presence of a gas, spill of a substance (for example, medication, drink, etc.), vomit, urine, feces, sweat, etc. In another example, a thermal camera associated with an OU 102 or AOU 130 can be calibrated against three sensor temperature readings (for example, itself, a thermal image, and ambient temperature to provide object temperature measurements of up to 0.25 C in precision). As will be appreciated by those of ordinary skill in the art, various applications can perform calibration and determination for a multitude of parameters consistent with this disclosure, all of which are considered to be within the scope of this disclosure.

While current monitoring devices only provide images/sound to an observer, in typical implementations, the MMOS 100 can alert multiple RU 140 (or other components of the MMOS 100—such as an OU 102 or AOU 130) if one or more monitored parameters (for example, temperature, position, breathing rate, audio, humidity, olfactory condition, etc.) exceed a preset or dynamically determined threshold.

In some implementations, one or more of the OU 102, AOU 130, and RU 140 of the MMOS 100 can be configured to interface with a cellular (or other network) to send SMS or MMS messages, emails, VOIP sessions, generate automated telephone calls (for example, to emergency personnel, observers, etc.). The MMOS 100 can also generate any other type of communication consistent with this disclosure.

At a high-level and in typical implementations, an OU 102 is a sensory computing device used in the MMOS 100 to provide general sensor data to one or more components of the MMOS 100. For example, in typical implementations, the OU 102 is placed relatively proximate to a subject to be observed/monitored (for example, a table, shelf, clipped to a light/mobile, attached to a bracket mounted on a wall, etc.). Depending on the type of sensor(s) the OU 102 is configured with, the OU 102 may need to be positioned nearer or farther from the subject. In the case of an OU 102 with an audio sensor (microphone) used for detecting the sounds of breathing, the OU 102 may need to be position relatively near to the subject. However, in the case of an OU 102 with a thermal imaging sensor (for example, an infrared (IR) thermal camera) used to determine overall skin temperature and/or breathing patterns/temperature of exhaled breath, the OU 102 can likely be placed at a greater relative distance from the subject.

At a high-level and in typical implementations, an AOU 130 is a sensory computing device used in the MMOS 100 to provide more precise sensor data than an OU 102 to one or more components of the MMOS 100. Typically, an AOU 130 will be communicatively coupled with one or more OUs 102, but can also be communicatively coupled with an RU 140. Although illustrated in FIG. 1 that an AOU 130 is coupled to the MMOS 100 (and to the OU 102) using network 160, in some implementations, the AOU 130 can be coupled directly to the illustrated OU 102 or to the RU 140 using, for example, WIFI, BLUETOOTH, a physical connector (for example, a cable or wire), and/or other transmission means consistent with this disclosure.

In a typical example of use, an OU 102 with a thermal imaging camera is mounted on wall bracket and aimed toward an observed subject lying in a bed. Additionally, a first AOU 130 with a heart rate sensor can be attached to the underside of the subject's mattress to gather and to provide heart rate data, a second wearable AOU 130 with a temperature sensor (for example, a digital thermometer) can be taped to the armpit area of the subject to gather temperature data, and a third AOU 130 can be taped to the subject's chest to detect breathing rate and an amount of chest elevation per breath (for example, using an accelerometer and/or a gyroscopic sensors). The first, second, and third AOUs 130 can provide their gathered data to the OU 102 for additional correlation, processing, analysis, transfer to an RU 140, etc.

In some implementations, and where appropriate, an OU 102 can be tasked as an AOU 130. For example, a first OU 102 could be communicatively coupled with a second OU 102, and the second OU 102 can be configured (for example using a user interface (UI)) associated with the first or second OU 102 or an RU 140 to act as an AOU 130. The second OU 102 could be attached to the bars of baby crib and a microphone configured with the second OU 102 can be used to monitor breathing regularity and clarity (for example, whether breathing is raspy, etc.), coughing, whether vomiting has occurred, etc.

At a high-level and in typical implementations, a RU 140 is a sensory computing device used in the MMOS 100 to provide an interface for an observer/monitor as to the condition/health of an observed/monitored subject. The RU 140 is, in typical implementations, a mobile or other computing device (for example, televisions (picture-in-picture and other modes), smart phones, tablet computers, wearable computers (such as head-mounted smart device such as GOOGLE GLASS), smart watches, and/or laptop computers) that can interface with an OU 102 or an AOU 130. The RU 140 typically acts as a controlling element in the MMOS 100. For example, the RU 140 can provide a graphical UI (GUI) used to configure various aspects of one or more of the RU 140, OU 102, AOU 130, and/or network 160. For example, configuration of the RU 140 can include setting alert parameter thresholds, data logging policies, whether the RU 140 displays thermal and/or daylight visual images, enabling and disabling audio communication, enabling and disabling various elements and features associated with the MMOS 100, and/or the like. As will be appreciated by those of ordinary skill in the art, there is a multitude of possible configuration for the described elements of the MMOS 100. It is noted that any configurations consistent with this disclosure are considered to be within the scope of the disclosure.

Figure 2:
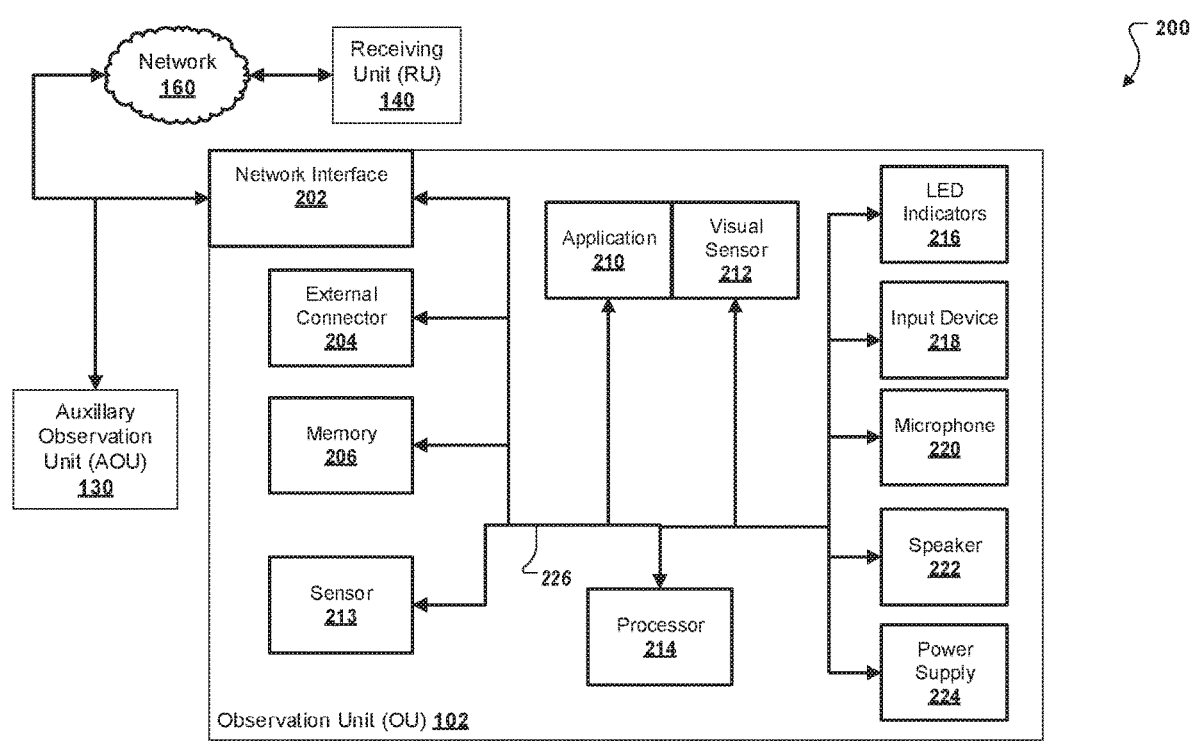
FIG. 2 illustrates a low-level view of an observation unit (OU) as an element of the MMOS of FIG. 1 according to an implementation.

FIG. 2 illustrates a low-level system view 200 of an observation unit (OU) 102 as an element of the MMOS 100 of FIG. 1 according to an implementation. In typical implementations, the OU 102 includes a network interface 202, external connector 204, memory 206, application 210, visual sensor 212, processor 214, LED indicators 216, input device 218, microphone 220, speaker 222, and power supply 224 communicating across a system bus 226. Note that while the OU 102 is illustrated in a particular example configuration in FIG. 2, the OU 102 is not limited by the illustrated implementation. As will be apparent to those of ordinary skill in the art, there are many possible configurations of the OU 102 consistent with this disclosure and the following descriptions. Other configurations consistent with this disclosure are considered to be within the scope of this disclosure. For example, in other implementations, the OU 102 can contain more or fewer components and/or the communicative coupling can be provided by more than one system bus 226.

The OU 102 includes a network interface 202. Although illustrated as a single interface 202 in FIG. 2, two or more network interfaces 202 may be used according to particular needs, desires, or particular implementations of the OU 102 and/or MMOS 100. The network interface 202 is used by the OU 102 for communicating with other systems (whether illustrated or not) in a distributed environment—including within the MMOS 100—connected to the network 160. Generally, the network interface 202 comprises logic encoded in software and/or hardware in a suitable combination and operable to communicate with the network 160. More specifically, the network interface 202 may comprise software supporting one or more communication protocols associated with communications such that the network 160 or interface's hardware is operable to communicate physical signals within and outside of the illustrated OU 102.

External connector 204 represents and can be configured as one or more of a removable memory (for example, flash memory, etc.) interface to allow the use of removable memory (not illustrated), a power supply connector, data transfer interface (for example, a USB, FIREWIRE, ETHERNET, or other data transfer interface), and the like. Although illustrated as a single external connector 204 in FIG. 2, two or more external connectors 204 may be used according to particular needs, desires, or particular implementations of the OU 102 and/or MMOS 100.

Memory 206 holds data for the OU 102 and/or the one or more elements of the MMOS 100 and represents both internal- and external (removable)-type memory used with the OU 102 and consistent with this disclosure. For example, internal-type memory can include one or more of flash, LPDDR2, and the like. External (removable)-type memory can include, for example, USB memory sticks, CF cards, SD cards, and the like. Although illustrated as a single memory 206 in FIG. 2, two or more memories 206 may be used according to particular needs, desires, or particular implementations of the OU 102 and/or MMOS 100.

The application 210 is an algorithmic software engine providing functionality according to particular needs, desires, or particular implementations of the OU 102 and/or performing any required functionality associated with the MMOS 100 and within the scope if this disclosure. For example, application 210 can provide functionality for one or more elements of the OU 102 described with respect to FIG. 2. Examples of this functionality can include gathering both thermal and daylight images using the visual sensor 212, correlating the images, and sending the correlated images across network 160 to the RU 140. Image recognition of varying degrees can also be performed by the application 210 and data sent across network 160 to the RU 140. In another example, application 210 can provide OU 102 functionality for two-way communication between the OU 102 and an RU 140. Further, although illustrated as a single application 210, the application 210 may be implemented as multiple applications 210 on the OU 102. In addition, although illustrated as integral to the OU 102, in alternative implementations, the application 210 can be external to the OU 102 and/or the MMOS 100.

Visual sensor 212 typically includes one or more of still/motion daylight, IR, ultraviolet (UV), or other spectrum cameras. For example, the visual sensor 212 can be implemented using a FLIR LEPTON thermal imager and a daylight high-definition (HD) imager. In some implementations, both an IR thermal image and a HD daylight image can be merged to produce a more useful low-light image for an observer and for image recognition and/or analysis (for example, by the application 210 and/or the RU 140). In some implementations, the OU 102 can include metadata with gathered still/motion images (for example, time, date, geographic location, time span, security data, observer identification, subject identification, and the like). In some implementations, audio (for example, gathered from microphone 220) can be added to images gathered using the visual sensor 212. Furthermore, although illustrated as a single visual sensor 212, the visual sensor 212 may be implemented as multiple visual sensors 212 on the OU 102. In addition, although illustrated as integral to the OU 102, in alternative implementations, the visual sensor 212 can be external to the OU 102 and/or the MMOS 100.

Sensor 213 typically includes one or more sensors gathering data related to humidity, atmospheric pressure, movement, ambient temperature, light exposure/level, olfactory condition, and/or other data consistent with this disclosure. The sensor 213 provides additional information about the ambient environment and/or condition of an observed/monitored subject. In some implementations, the OU 102 can include metadata with gathered data from sensor 213 (for example, time, date, geographic location, time span, security data, observer identification, subject identification, and the like). Furthermore, although illustrated as a single sensor 213, the sensor 213 may be implemented as multiple sensors 213 on the OU 102. In addition, although illustrated as integral to the OU 102, in alternative implementations, the sensor 213 can be external to the OU 102 and/or the MMOS 100.

The OU 102 includes a processor 214. Although illustrated as a single processor 214 in FIG. 2, two or more processors may be used according to particular needs, desires, or particular implementations of the OU 102 and/or the MMOS 100. Generally, the processor 214 executes instructions and manipulates data to perform the operations (include those described above) performed by the OU 102. Specifically, the processor 214 can execute the functionality for creating, operating, and/or managing an OU 102 and/or MMOS 100 (or any element of the MMOS 100) and/or performing any functionality associated with the MMOS 100 and within the scope of this disclosure. In some implementations, the processor can be configured as a system-on-a-chip (SoC), system-in-parts (SiP), or other configuration (for example, including a memory controller, processor, graphics processor, memory, memory interface, network interface, and the like in a single or tightly-integrated package). In these implementations, various described elements of the OU 102 can be incorporated into and performed by the processor 214.

In some implementations, the OU 102 can include a light-emitting-diode (LED) indicator 216 to provide visual indications to a user. For example, the LED indicator 216 can indicate a visual image or audio data is being gathered, an alarm condition has been initiated, battery power is low, and the like. In some implementations, the LED indicator 216 can be configured to flash in different colors, different patterns, etc. depending on data to be conveyed.

In some implementations, the input device 218 can include a built-in keyboard, keypad, touch-sensitive display, verbal command recognition (for example, using the microphone 220 and/or an external device such as a smart phone or smart watch connected/paired to the OU 102 to gather voice data for command recognition), and the like. In some implementations, desired functionality may need to be entered using more than one input device 218.

Microphone 220 provides audio input functionality, while speaker 222 provides audio output functionality. In some implementations, the microphone 220 and or speaker 222 can include externally connected (for example, using external connector 204) microphones 220 and/or speakers 222 to provide better audio input/output resolution.

In some implementations, power supply 224 can include AC/DC, battery, rechargeable battery, and/or other power sources used to operate the OU 102. Power supply 224 is typically interfaced with at least one form of power switch to turn the device ON/OFF (for example, button, toggle, touch-sensitive, voice control, etc.). In some implementations, the OU 102 provides functionality to analyze and inform a user of the charge/recharge status of batteries. In some configurations, rechargeable batteries can either be user- or non-user-replaceable.

Figure 3:
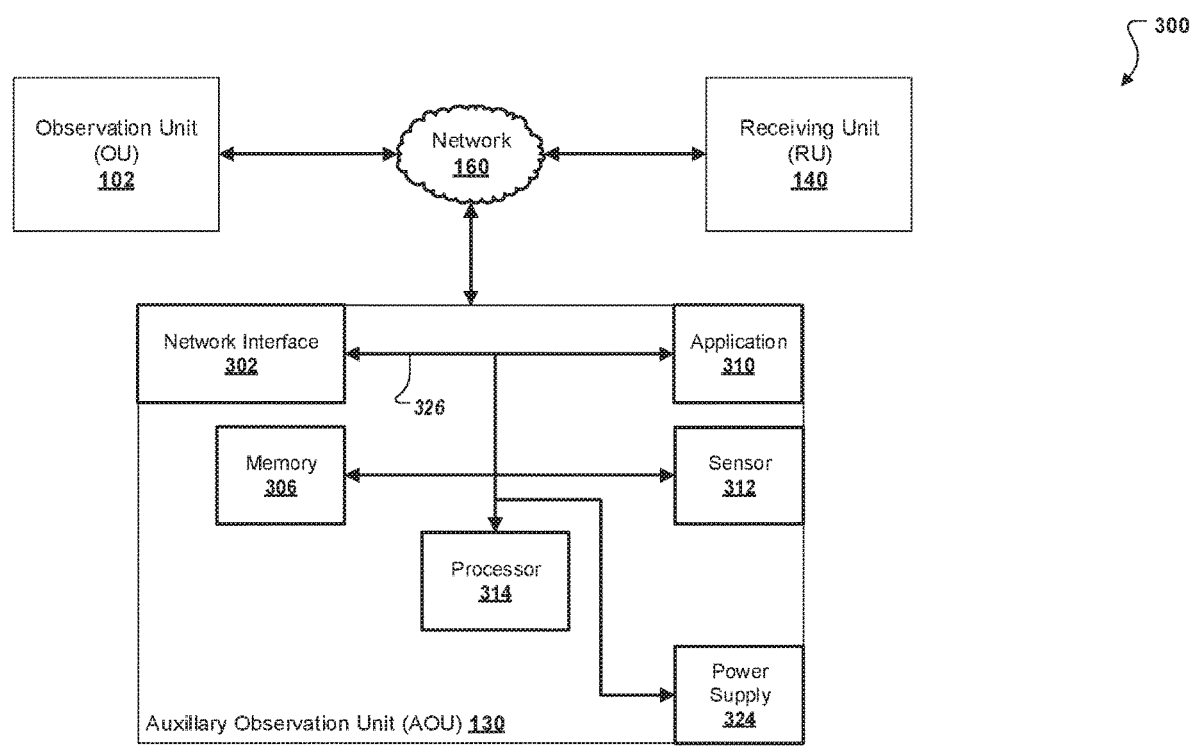
FIG. 3 illustrates a low-level view of an auxiliary observation unit (AOU) as an element of the MMOS of FIG. 1 according to an implementation.

FIG. 3 illustrates a low-level view 300 of an auxiliary observation unit (AOU) 130 as an element of the MMOS 100 of FIG. 1 according to an implementation. In typical implementations, the AOU 130 includes a network interface 302, memory 306, application 310, sensor 312, processor 314, and power supply 324 communicating across a system bus 326. Note that while the AOU 130 is illustrated in a particular example configuration in FIG. 3, the AOU 130 is not limited by the illustrated implementation. As will be apparent to those of ordinary skill in the art, there are many possible configurations of the AOU 130 consistent with this disclosure and the following descriptions. Other configurations consistent with this disclosure are considered to be within the scope of this disclosure. For example, in other implementations, the AOU 130 can contain more or fewer components and/or the communicative coupling can be provided by more than one system bus 326.

The AOU 130 includes a network interface 302. Although illustrated as a single interface 302 in FIG. 3, two or more network interfaces 302 may be used according to particular needs, desires, or particular implementations of the AOU 130 and/or MMOS 100. The network interface 302 is used by the AOU 130 for communicating with other systems (whether illustrated or not) in a distributed environment—including within the MMOS 100—connected to the network 160. Generally, the network interface 302 comprises logic encoded in software and/or hardware in a suitable combination and operable to communicate with the network 160. More specifically, the network interface 302 may comprise software supporting one or more communication protocols associated with communications such that the network 160 or interface's hardware is operable to communicate physical signals within and outside of the illustrated AOU 130.

Memory 306 holds data for the AOU 130 and/or the one or more elements of the MMOS 100 and represents both internal- and external (removable)-type memory used with the AOU 130 and consistent with this disclosure. For example, internal-type memory can include one or more of flash, LPDDR2, and the like. External (removable)-type memory can include, for example, USB memory sticks, CF cards, SD cards, and the like. Although illustrated as a single memory 306 in FIG. 3, two or more memories 306 may be used according to particular needs, desires, or particular implementations of the AOU 130 and/or MMOS 100.

The application 310 is an algorithmic software engine providing functionality according to particular needs, desires, or particular implementations of the AOU 130 and/or performing any required functionality associated with the MMOS 100 and within the scope of this disclosure. For example, application 310 can provide functionality for one or more elements of the AOU 130 described with respect to FIG. 3. Examples of this functionality can include gathering particular data from sensor 312 (for example, heartbeat detection, chest rise/fall, etc.) and sending the gathered sensor data across network 160 to the OU 102 and/or RU 140. Further, although illustrated as a single application 310, the application 310 may be implemented as multiple applications 310 on the AOU 130. In addition, although illustrated as integral to the AOU 130, in alternative implementations, the application 310 can be external to the AOU 130 and/or the MMOS 100.

Sensor 312 can detect various types of data related to an observed/monitored subject. Example sensors can include those gathering audio, temperature, motion, humidity, atmospheric pressure, olfactory condition, image data (for example, similar to OU 102 functionality including image processing) and the like. In some implementations, the AOU 130 can include metadata with gathered sensor data (for example, time, date, geographic location, time span, security data, observer identification, subject identification, and the like). Furthermore, although illustrated as a single sensor 312, the sensor 312 may be implemented as multiple sensors 312 on the AOU 130. In addition, although illustrated as integral to the AOU 130, in alternative implementations, the sensor 312 can be external to the AOU 130 and/or the MMOS 100.

The AOU 130 includes a processor 314. Although illustrated as a single processor 314 in FIG. 3, two or more processors may be used according to particular needs, desires, or particular implementations of the AOU 130 and/or the MMOS 100. Generally, the processor 314 executes instructions and manipulates data to perform the operations (include those described above) performed by the AOU 130. Specifically, the processor 314 can execute the functionality for creating, operating, and/or managing an AOU 130 and/or MMOS 100 (or any element of the MMOS 100) and/or performing any functionality associated with the MMOS 100 and within the scope of this disclosure. In some implementations, the processor can be configured as a system-on-a-chip (SoC), system-in-parts (SiP), or other configuration (for example, including a memory controller, processor, graphics processor, memory, memory interface, network interface, and the like in a single or tightly-integrated package). In these implementations, various described elements of the AOU 130 can be incorporated into and performed by the processor 314.

In some implementations, power supply 324 can include AC/DC, battery, rechargeable battery, and/or other power sources used to operate the AOU 130. Power supply 324 is typically interfaced with at least one form of power switch to turn the device ON/OFF (for example, button, toggle, touch-sensitive, voice control, etc.). In some implementations, the AOU 130 provides functionality to analyze and inform a user of the charge/recharge status of batteries (for example, through the OU 102 and/or RU 140). In some configurations, rechargeable batteries can either be user- or non-user-replaceable.

Figure 4:
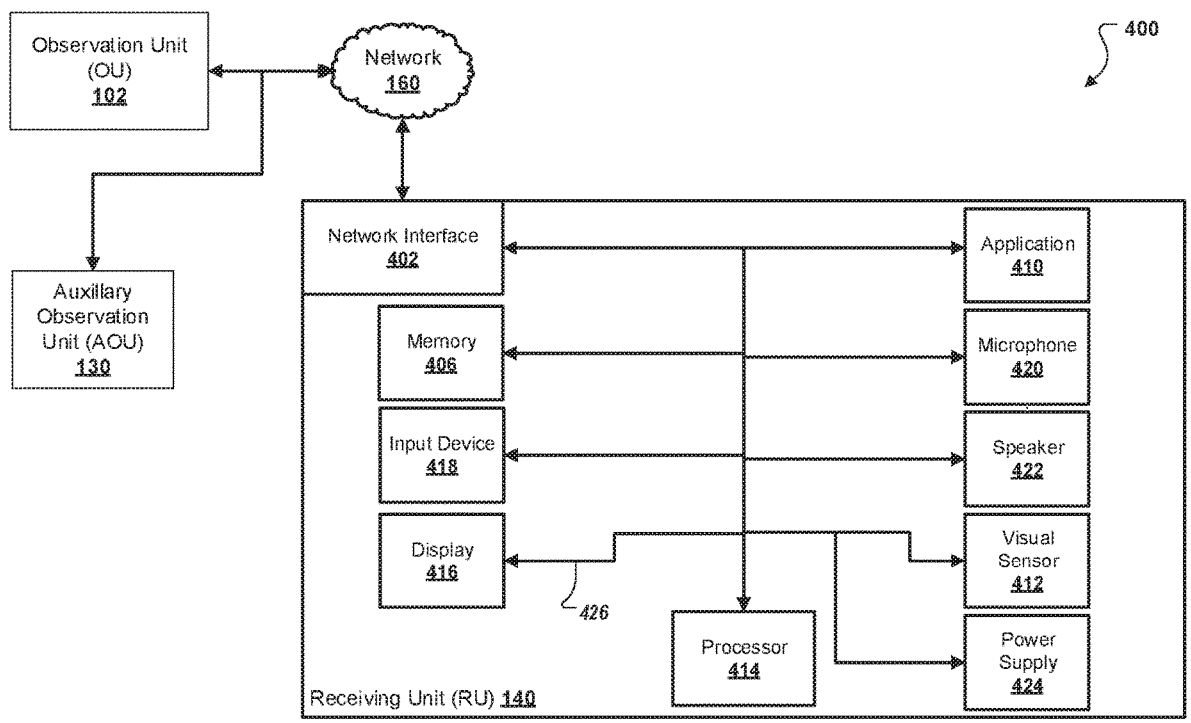
FIG. 4 illustrates a low-level view of an axillary observation unit (AOU) as an element of the MMOS of FIG. 1 according to an implementation.

FIG. 4 illustrates a low-level view 400 of a receiving unit (RU) 140 as an element of the MMOS of FIG. 1 according to an implementation. In typical implementations, the RU 140 includes a network interface 402, memory 406, application 410, visual sensor 412, processor 414, display 416, input device 418, microphone 420, speaker 422, and power supply 424 communicating across a system bus 426. Note that while the RU 140 is illustrated in a particular example configuration in FIG. 4, the RU 140 is not limited by the illustrated implementation. As will be apparent to those of ordinary skill in the art, there are many possible configurations of the RU 140 consistent with this disclosure and the following descriptions. Other configurations consistent with this disclosure are considered to be within the scope of this disclosure. For example, in other implementations, the RU 140 can contain more or fewer components and/or the communicative coupling can be provided by more than one system bus 426.

The RU 140 includes a network interface 402. Although illustrated as a single interface 402 in FIG. 4, two or more network interfaces 402 may be used according to particular needs, desires, or particular implementations of the RU 140 and/or MMOS 100. The network interface 402 is used by the RU 140 for communicating with other systems (whether illustrated or not) in a distributed environment—including within the MMOS 100—connected to the network 160. Generally, the network interface 402 comprises logic encoded in software and/or hardware in a suitable combination and operable to communicate with the network 160. More specifically, the network interface 402 may comprise software supporting one or more communication protocols associated with communications such that the network 160 or interface's hardware is operable to communicate physical signals within and outside of the illustrated RU 140.

Memory 406 holds data for the RU 140 and/or the one or more elements of the MMOS 100 and represents both internal- and external (removable)-type memory used with the RU 140 and consistent with this disclosure. For example, internal-type memory can include one or more of flash, LPDDR2, and the like. External (removable)-type memory can include, for example, USB memory sticks, CF cards, SD cards, and the like. Although illustrated as a single memory 406 in FIG. 4, two or more memories 406 may be used according to particular needs, desires, or particular implementations of the RU 140 and/or MMOS 100.

The application 410 is an algorithmic software engine providing functionality according to particular needs, desires, or particular implementations of the RU 140 and/or performing any required functionality associated with the MMOS 100 and within the scope if this disclosure. For example, application 410 can provide functionality for one or more elements of the RU 140 described with respect to FIG. 4. Examples of this functionality can include gathering a visual image using the visual sensor 412 and transmitting it to the OU 102 over network 160 for two-way communication with the subject. Image recognition of varying degrees can also be performed by the application 410 using image data received from one or more OUs 102/AOUs 130 across network 160. Furthermore, although illustrated as a single application 410, the application 410 may be implemented as multiple applications 410 on the RU 140. In addition, although illustrated as integral to the RU 140, in alternative implementations, the application 410 can be external to the RU 140 and/or the MMOS 100.

Visual sensor 412 typically includes one or more of still/motion daylight, IR, ultraviolet (UV), or other spectrum cameras. For example, the visual sensor 412 can be implemented using a FLIR LEPTON thermal imager and a daylight high-definition (HD) imager. In some implementations, both an IR thermal image and a HD daylight image can be merged to produce a more useful low-light image for an observer and for image recognition and/or analysis (for example, by the application 410 and/or the OU 102/AOU 130). In some implementations, the RU 140 can include metadata with gathered still/motion images (for example, time, date, geographic location, time span, security data, observer identification, subject identification, and the like). In some implementations, audio (for example, gathered from microphone 320) can be added to images gathered using the visual sensor 312. Further, although illustrated as a single visual sensor 312, the visual sensor 312 may be implemented as multiple visual sensors 312 on the RU 140. In addition, although illustrated as integral to the RU 140, in alternative implementations, the visual sensor 312 can be external to the RU 140 and/or the MMOS 100.

The RU 140 includes a processor 314. Although illustrated as a single processor 314 in FIG. 4, two or more processors may be used according to particular needs, desires, or particular implementations of the RU 140 and/or the MMOS 100. Generally, the processor 314 executes instructions and manipulates data to perform the operations (include those described above) performed by the RU 140. Specifically, the processor 314 can execute the functionality for creating, operating, and/or managing an RU 140 and/or MMOS 100 (or any element of the MMOS 100) and/or performing any functionality associated with the MMOS 100 and within the scope of this disclosure. In some implementations, the processor can be configured as a system-on-a-chip (SoC), system-in-parts (SiP), or other configuration (for example, including a memory controller, processor, graphics processor, memory, memory interface, network interface, and the like in a single or tightly-integrated package). In these implementations, various described elements of the RU 140 can be incorporated into and performed by the processor 314.

In some implementations, the RU 140 can include a display 416 (for example, LCD, OLED, and the like) to provide both visual indications and data to an observer/monitor and to accept user input from the observer/monitor. For example, the display 416 can display a visual image, provide a GUI, display processed data in graphical form (for example, in charts/graphs), and the like.

In some implementations, the input device 418 can include a built-in keyboard, keypad, touch-sensitive display, verbal command recognition (for example, using the microphone 420 and/or an external device such as a smart phone or smart watch connected/paired to the RU 140 to gather voice data for command recognition), and the like. In some implementations, desired functionality may need to be entered using more than one input device 418.

Microphone 420 provides audio input functionality, while speaker 422 provides audio output functionality. In some implementations, the microphone 420 and or speaker 422 can include externally connected (for example, using a non-illustrated external connector) microphones 420 and/or speakers 422 to provide better audio input/output resolution.

In some implementations, power supply 424 can include AC/DC, battery, rechargeable battery, and/or other power sources used to operate the RU 140. Power supply 424 is typically interfaced with at least one form of power switch to turn the device ON/OFF (for example, button, toggle, touch-sensitive, voice control, etc.). In some implementations, the RU 140 provides functionality to analyze and inform a user of the charge/recharge status of batteries. In some configurations, rechargeable batteries can either be user- or non-user-replaceable.

In some implementations, the OU 102, AOU 130, and/or the RU 140 internal system bus 226, casing, data interfaces, application 210, and the like can be configured to permit modular addition/removal of components from the OU 102, AOU 130, and/or the RU 140. For example, an OU 102 can be configured with some standard components (for example, memory 206, application 210, processor 214, input device 218, etc.), but other elements of OU 102 can be modularly added and removed from the OU 102, AOU 130, and/or RU 140. For example, in a modular OU 102, the visual sensors 212 can be replaced for better resolution or to gather different spectrum images (for example, ultraviolet, infrared, etc.), a directional microphone 220, stereo speaker 222, and an enhanced power supply 224.

Although not illustrated with respect to FIGS. 1-4, each of the OU 102, AOU 130, and/or RU 140 can be configured with appropriate mechanisms to permit resting, aiming, attaching, securing, etc. the OU 102, AOU 130, and/or RU 140 to various surfaces, structures, body parts, etc. For example, the AOU 130 can be configured with a strap (for example, to attach to a wrist or ankle), clip (for example, to attach to clothing or bedding), adhesive (for example, to attach the AOU 130 to a wall, bed post, crib bar, etc.). Other attachment mechanisms can include brackets, adhesive (for example, double-sided tape), elastic bands, screws, hooks, laces, ties, hook-and-loop tape (for example, VELCRO), bolts/nuts, and the like consistent with this disclosure.

It should be noted that FIGS. 1-4 illustrate one possible implementation of an OU 102, AOU 130, RU 140, and network 160. In some implementations, elements not present/described with respect to either the OU 102, AOU 130, RU 140, and/or network 160 in FIGS. 1-4 can be associated with either of the OU 102, AOU 130, RU 140, and/or network 160. For example, while the AOU 130 is not described in FIG. 3 as being configured with LED indicators, an input device, or a display as are the OU 102 and RU 140 in FIGS. 2 and 4, respectively, in some implementations, an AOU 130 can be configured with one or more of these elements. In fact, as described above, an OU 102 can be tasked and configured to operate as an AOU 130. As will be appreciated by those of ordinary skill in the art, the OU 102, AOU 130, RU 140, and/or network 160 can have many possible configurations, sensors, associated functionality, etc. Any configuration of an OU 102, AOU 130, RU 140, network 160, and/or other element of the described MMOS 100 consistent with this disclosure is considered to be within the scope of this disclosure.

Figure 5:
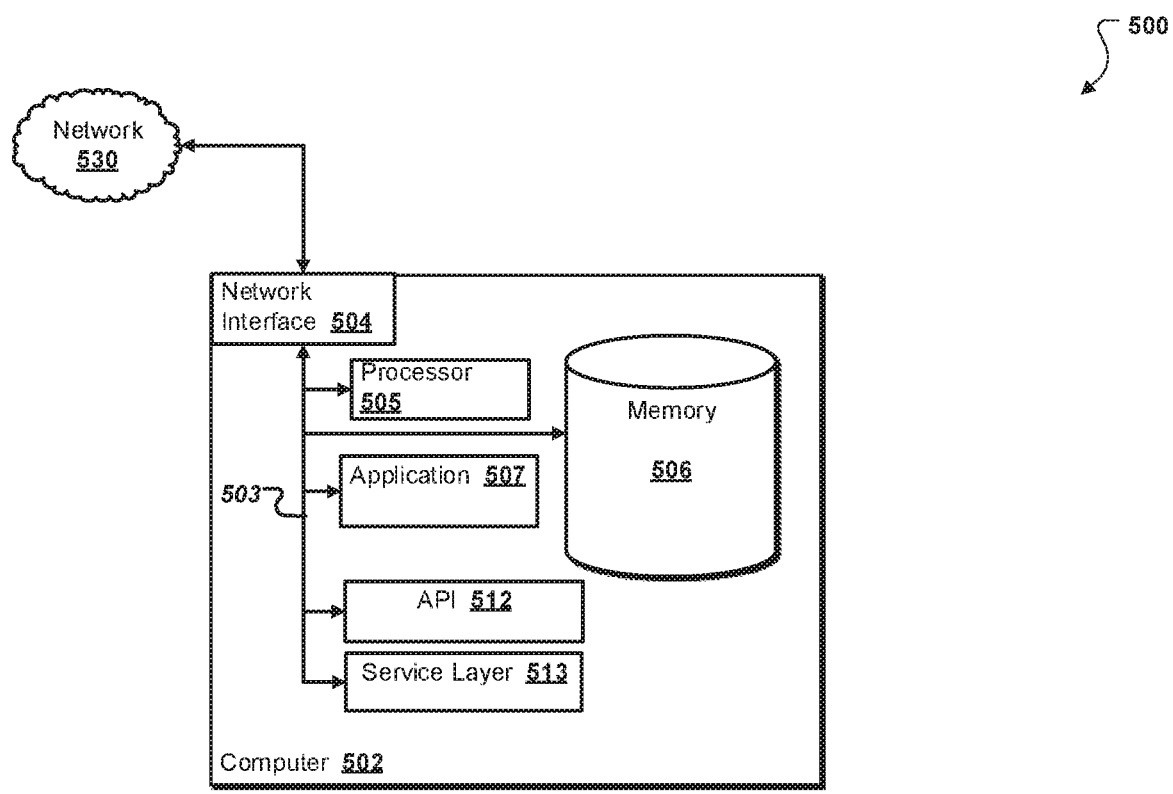
FIG. 5 is a block diagram illustrating an exemplary computer used in the MMOS according to an implementation.

FIG. 5 is a block diagram 500 illustrating an exemplary computer 502 used in the MMOS 100 according to an implementation. The illustrated computer 502 is intended to encompass any computing device such as a server, desktop computer, laptop/notebook computer, wireless data port, smart phone, personal data assistant (PDA), tablet computing device, wearable computer, smart watch, television, one or more processors within these devices, or any other suitable processing device, including both physical and/or virtual instances of the computing device. Additionally, the computer 502 may comprise a computer that includes an input device, such as a keypad, keyboard, touch screen, or other device that can accept user information, and an output device that conveys information associated with the operation of the computer 502, including digital data, visual and/or audio information, or a GUI.

While the computer 502 typically serves as a OU 102, AOU 130, and/or RU 140, in some implementations, the computer 502 can also serve as a client, network component, a server, a database or other persistency, and/or any other component (whether or not illustrated) of the MMOS 100. The illustrated computer 502 is communicably coupled with a network 530 (for example, network 160 of FIGS. 1 and 2A-2C). In some implementations, one or more components of the computer 502 may be configured to operate within a cloud-computing-based environment.

At a high level, the computer 502 is an electronic computing device operable to receive, transmit, process, store, or manage data and information associated with the MMOS 100. In some implementations, the computer 502 may also include or be communicably coupled with an application server, e-mail server, web server, caching server, streaming data server, business intelligence (BI) server, and/or other server.

The computer 502 can receive requests over network 530 from an application (for example, an application 507 executing on another computer 502 or another application) and responding to the received requests by processing the said requests in an application (for example, application 507). In addition, requests may also be sent to the computer 502 from internal users (for example, from a command console or by other appropriate access method), external or third-parties, other automated applications, as well as any other appropriate entities, individuals, systems, or computers.

Each of the components of the computer 502 can communicate using a system bus 503. In some implementations, any and/or all the components of the computer 502, both hardware and/or software, may interface with each other and/or the network interface 504 over the system bus 503 using an application programming interface (API) 512 and/or or a service layer 513. The API 512 may include specifications for routines, data structures, and object classes. The API 512 may be either computer-language dependent/independent and refer to a complete interface, a single function, or even a set of APIs. The service layer 513 provides software services to the computer 502 and/or the MMOS 100. The functionality of the computer 502 may be accessible for all service consumers using this service layer. Software services, such as those provided by the service layer 513, provide reusable, defined business functionalities through a defined interface. For example, the interface may be software written in JAVA, C++, or other suitable language providing data in extensible markup language (XML) format or other suitable format. While illustrated as an integrated component of the computer 502, alternative implementations may illustrate the API 512 and/or the service layer 513 as stand-alone components in relation to other components of the computer 502 and/or MMOS 100. Moreover, any or all parts of the API 512 and/or the service layer 513 may be implemented as child or sub-modules of another software module, application, or hardware module without departing from the scope of this disclosure.

The computer 502 includes a network interface 504. Although illustrated as a single network interface 504 in FIG. 5, two or more interfaces 504 may be used according to particular needs, desires, or particular implementations of the computer 502 and/or MMOS 100. The network interface 504 is used by the computer 502 for communicating with other systems (whether illustrated or not) in a distributed environment—including within the MMOS 100—connected to the network 530. Generally, the network interface 504 comprises logic encoded in software and/or hardware in a suitable combination and operable to communicate with the network 530. More specifically, the network interface 504 may comprise software supporting one or more communication protocols associated with communications such that the network 530 or interface's hardware is operable to communicate physical signals within and outside of the illustrated MMOS 100.

The computer 502 includes a processor 505. Although illustrated as a single processor 505 in FIG. 5, two or more processors may be used according to particular needs, desires, or particular implementations of the computer 502 and/or the MMOS 100. Generally, the processor 505 executes instructions and manipulates data to perform the operations of the computer 502. Specifically, the processor 505 can execute the functionality for creating, operating, and/or managing a MMOS 100 (or any element of the MMOS 100) and/or performing any functionality associated with the MMOS 100 and within the scope of this disclosure.

The computer 502 also includes a memory 506 that holds data for the computer 502 and/or other components of the MMOS 100. Although illustrated as a single memory 506 in FIG. 5, two or more memories may be used according to particular needs, desires, or particular implementations of the computer 502 and/or the MMOS 100. While memory 506 is illustrated as an integral component of the computer 502, in alternative implementations, memory 506 can be external to the computer 502 and/or the MMOS 100.

The application 507 is an algorithmic software engine providing functionality according to particular needs, desires, or particular implementations of the computer 502, particularly with respect to functionality required for creating, operating, and/or managing a MMOS 100 (or any element of the MMOS 100) and/or performing any functionality associated with the MMOS 100 and within the scope of this disclosure. For example, application 507 can provide functionality for one or more components, modules, applications, etc. described with respect to FIGS. 1 and 2A-2C, and/or FIG. 4. Further, although illustrated as a single application 507, the application 507 may be implemented as multiple applications 507 on the computer 502. In addition, although illustrated as integral to the computer 502, in alternative implementations, the application 507 can be external to the computer 502 and/or the MMOS 100.

There may be any number of computers 502 associated with, or external to, the MMOS 100 and communicating over network 530. Further, the term "client," "user," and other appropriate terminology may be used interchangeably as appropriate without departing from the scope of this disclosure. Moreover, this disclosure contemplates that many users may use one computer 502, or that one user may use multiple computers 502.

FIG. 6 is a flow chart of a method 600 of use of the MMOS 100 according to an implementation.

For clarity of presentation, the description that follows generally describes method 600 in the context of FIGS. 1-5. However, it will be understood that method 600 may be performed, for example, by any other suitable system, environment, software, and hardware, or a combination of systems, environments, software, and hardware as appropriate. In some implementations, various steps of method 600 can be run in parallel, in combination, in loops, or in any order.

At 602, observation unit (OU) and auxiliary observation unit (AOU) sensors are calibrated (for example, as described above) in relation to an ambient environment. In typical implementations, calibration in relation to the ambient environment includes data related to at least one of audio, temperature, pressure, light level, humidity, or olfactory condition. In some implementations, thermal calibration can be performed using a particular thermal sensor itself, a thermal image, and an ambient environmental temperature. From 602, method 600 proceeds to 604.

At 604, the OU and AOU sensors are calibrated (as described above) in relation to an observational subject. In typical implementations, calibration in relation to the observational subject includes at least one of a particular subject, normal skin temperature, normal breath temperature, breath regularity, breath clarity, chest rise or fall, heart rate, heart regularity, or various body positions using position mapping. From 604, method 600 proceeds to 606.

At 606, monitoring parameters for the calibrated sensors are established using a receiving unit (RU). For example, monitoring parameters can include degrees of temperature, humidity, noise, subject positions, heart rate, breathing rate, etc. From 606, method 600 proceeds to 608.

At 608, monitoring types are activated using the RU. For example, for a particular subject, an observer may only wish to monitor heart rate and temperature. The RU can be used to activate these particular monitoring types while excluding others. In some implementations, the other monitoring types can be set to auto trigger if an "extreme" situation occurs (for example, using a separate set of monitoring parameters as in 606). For example, if the subjects breathing stops, but the heart is still beating, an observer can be alerted immediately. From 608, method 600 proceeds to 610.

At 610, data is gathered using the OU and AOUs. From 610, method 600 proceeds to 612.

At 612, a determination is made whether any of the gathered data exceeds thresholds for established monitoring parameters. In some implementations, metadata can be added to gathered sensor data from the OU, AOU, or RU sensors. In these implementations, metadata can include at least one of time, date, geographic location, time span, security data, observer identification, or subject identification. Determinations can be made on one or more of the OU, AOU, and RU. For example, image data can be gathered by an OU and transferred to the RU for image analysis/processing and a determination that a monitoring parameter has been exceeded. In other implementations, the OU can process received images and if an alert threshold is determined to be exceeded, send an alert signal to the RU. If NO, 612 proceeds back to 610 where data continues to be gathered. If YES, 612 proceeds to 614.

At 614, alerts are generated. In some implementations, alerts can be generated on one or more of the RU, the OU, and the AOU. For example, audio alarms, light, strobe effects, various communications (as described above), etc. can be triggered. An observer can then investigate and take mitigating action if necessary and/or reset/silence the generated alarms (for example, using a GUI associated with the RU, OU, and/or AOU). After 614, method 600 proceeds back to 612 to gather data. As will be appreciated by those of ordinary skill in the art, there are a multitude of possible functions that can be performed with and using data received by elements of the MMOS 100 the smart device application. The example provided in the context of FIG. 6 is meant to be merely instructive and is not meant to be limiting in any way.

Described implementations of the subject matter can include one or more features, alone or in combination.

For example, in a first implementation, a computer-implemented method includes: calibrating an observation unit (OU) and auxiliary observation unit (AOU) sensor in relation to an ambient environment; calibrating the OU sensor and the AOU sensor in relation to an observational subject; establishing, using a receiving unit (RU), monitoring parameters for the calibrated sensors; activating monitoring types using the RU; gathering data from the OU sensor and the AOU sensor; determining that the gathered data exceeds the established monitoring parameters; and generating one or more alerts based on the determination.

The foregoing and other described implementations can each optionally include one or more of the following features:

A first feature, combinable with any of the following features, wherein calibration in relation to the ambient environment includes data related to at least one of audio, temperature, pressure, light level, humidity, or olfactory condition.

A second feature, combinable with any of the previous or following features, wherein calibration in relation to the observational subject includes at least one of a particular subject, normal skin temperature, normal breath temperature, breath regularity, breath clarity, chest rise or fall, heart rate, heart regularity, or various body positions using position mapping.

A third feature, combinable with any of the previous or following features, wherein thermal calibration is performed using a particular thermal sensor itself, a thermal image, and an ambient environmental temperature.

A fourth feature, combinable with any of the previous or following features, comprising including metadata with gathered sensor data from the OU sensor, the AOU sensor, or the RU sensor.

A fifth feature, combinable with any of the previous or following features, wherein metadata can include at least one of time, date, geographic location, time span, security data, observer identification, or subject identification.

A sixth feature, combinable with any of the previous or following features, wherein the AOU sensor is worn on a body or placed on, in, or underneath a mattress.

In a second implementation, a non-transitory, computer-readable medium storing one or more instructions executable by a computer system to perform operations comprising: calibrating an observation unit (OU) and auxiliary observation unit (AOU) sensor in relation to an ambient environment; calibrating the OU sensor and the AOU sensor in relation to an observational subject; establishing, using a receiving unit (RU), monitoring parameters for the calibrated sensors; activating monitoring types using the RU; gathering data from the OU sensor and the AOU sensor; determining that the gathered data exceeds the established monitoring parameters; and generating one or more alerts based on the determination.

The foregoing and other described implementations can each optionally include one or more of the following features:

A first feature, combinable with any of the following features, wherein calibration in relation to the ambient environment includes data related to at least one of audio, temperature, pressure, light level, humidity, or olfactory condition.

A second feature, combinable with any of the previous or following features, wherein calibration in relation to the observational subject includes at least one of a particular subject, normal skin temperature, normal breath temperature, breath regularity, breath clarity, chest rise or fall, heart rate, heart regularity, or various body positions using position mapping.

A third feature, combinable with any of the previous or following features, wherein thermal calibration is performed using a particular thermal sensor itself, a thermal image, and an ambient environmental temperature.

A fourth feature, combinable with any of the previous or following features, comprising instructions to include metadata with gathered sensor data from the OU sensor, the AOU sensor, or the RU sensor.

A fifth feature, combinable with any of the previous or following features, wherein metadata can include at least one of time, date, geographic location, time span, security data, observer identification, or subject identification.

A sixth feature, combinable with any of the previous or following features, wherein the AOU sensor is worn on a body or placed on, in, or underneath a mattress.

In a third implementation, a computer system, comprising: a computer memory; and a hardware processor interoperably coupled with the computer memory and configured to perform operations comprising: calibrating an observation unit (OU) and auxiliary observation unit (AOU) sensor in relation to an ambient environment; calibrating the OU sensor and the AOU sensor in relation to an observational subject; establishing, using a receiving unit (RU), monitoring parameters for the calibrated sensors; activating monitoring types using the RU; gathering data from the OU sensor and the AOU sensor; determining that the gathered data exceeds the established monitoring parameters; and generating one or more alerts based on the determination.

The foregoing and other described implementations can each optionally include one or more of the following features:

A first feature, wherein calibration in relation to the ambient environment includes data related to at least one of audio, temperature, pressure, light level, humidity, or olfactory condition.

A second feature, combinable with any of the previous or following features, wherein calibration in relation to the observational subject includes at least one of a particular subject, normal skin temperature, normal breath temperature, breath regularity, breath clarity, chest rise or fall, heart rate, heart regularity, or various body positions using position mapping, and thermal calibration is performed using a particular thermal sensor itself, a thermal image, and an ambient environmental temperature.

A third feature, combinable with any of the previous or following features, configured to perform one or more operations including metadata with gathered sensor data from the OU sensor, the AOU sensor, or the RU sensor.

A fourth feature, combinable with any of the previous or following features, wherein metadata can include at least one of time, date, geographic location, time span, security data, observer identification, or subject identification.

A fifth feature, combinable with any of the previous or following features, wherein the AOU sensor is worn on a body or placed on, in, or underneath a mattress.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Implementations of the subject matter described in this specification can be implemented as one or more computer programs, that is, one or more modules of computer program instructions encoded on a tangible, non-transitory computer-storage medium for execution by, or to control the operation of, data processing apparatus. Alternatively or in addition, the program instructions can be encoded on an artificially generated propagated signal, for example, a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of one or more of them.

The terms "data processing apparatus," "computer," or "electronic computer device" (or equivalent as understood by one of ordinary skill in the art) refer to data processing hardware and encompass all kinds of apparatus, devices, and machines for processing data, including by way of example, a programmable processor, a computer, or multiple processors or computers. The apparatus can also be or further include special purpose logic circuitry, for example, a central processing unit (CPU), an FPGA (field programmable gate array), or an ASIC (application-specific integrated circuit). In some implementations, the data processing apparatus and/or special purpose logic circuitry may be hardware-based and/or software-based. The apparatus can optionally include code that creates an execution environment for computer programs, for example, code that constitutes processor firmware, a protocol stack, a database management system, an operating system, or a combination of one or more of them. The present disclosure contemplates the use of data processing apparatuses with or without conventional operating systems, for example, LINUX, UNIX, WINDOWS, MAC OS, ANDROID, IOS, or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third-party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, for example, a CPU, an FPGA, or an ASIC.

Computers suitable for the execution of a computer program can be based on general or special purpose microprocessors, both, or any other kind of CPU. Generally, a CPU will receive instructions and data from a read-only memory (ROM) or a random access memory (RAM) or both. The essential elements of a computer are a CPU for performing or executing instructions and one or more memory devices for storing instructions and data. Generally, a computer will also include, or be operatively coupled to, receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a global positioning system (GPS) receiver, or a portable storage device, for example, a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, for example, erasable programmable read-only memory (EPROM), electrically erasable programmable read-only memory (EEPROM), and flash memory devices; magnetic disks, for example, internal hard disks or removable disks; magneto-optical disks; and CD-ROM, DVD+/−R, DVD-RAM, and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, for example, a CRT (cathode ray tube), LCD (liquid crystal display), LED (Light Emitting Diode), or plasma monitor, for displaying information to the user and a keyboard and a pointing device, for example, a mouse, trackball, or trackpad by which the user can provide input to the computer. Input may also be provided to the computer using a touchscreen, such as a tablet computer surface with pressure sensitivity, a multi-touch screen using capacitive or electric sensing, or other type of touchscreen. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or "GUI," may be used in the singular or the plural to describe one or more graphical user interfaces and each of the displays of a particular graphical user interface. Therefore, a GUI may represent any graphical user interface including, but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, for example, as a data server, or that includes a middleware component, for example, an application server, or that includes a front-end component, for example, a client computer having a graphical user interface or a Web browser through which a user can interact with an implementation of the subject matter described in this specification, or any combination of one or more such back-end, middleware, or front-end components. The components of the system can be interconnected by any form or medium of wireline and/or wireless digital data communication, for example, a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n and/or 802.20, all or a portion of the Internet, and/or any other communication system or systems at one or more locations. The network may communicate with, for example, Internet Protocol (IP) packets, Frame Relay frames, Asynchronous Transfer Mode (ATM) cells, voice, video, data, and/or other suitable information between network addresses.

The computing system can include clients and servers. A client and server are generally remote from each other and typically interact through a communication network. The relationship of client and server arises by virtue of computer programs running on the respective computers and having a client-server relationship to each other.

In some implementations, any or all of the components of the computing system, both hardware and/or software, may interface with each other and/or the interface using an application programming interface (API) and/or a service layer. The API may include specifications for routines, data structures, and object classes. The API may be either computer language-independent or -dependent and refer to a complete interface, a single function, or even a set of APIs. The service layer provides software services to the computing system. The functionality of the various components of the computing system may be accessible for all service consumers using this service layer. Software services provide reusable, defined business functionalities through a defined interface. For example, the interface may be software written in JAVA, C++, or other suitable language providing data in extensible markup language (XML) format or other suitable format. The API and/or service layer may be an integral and/or a stand-alone component in relation to other components of the computing system. Moreover, any or all parts of the service layer may be implemented as child or sub-modules of another software module, application, or hardware module without departing from the scope of this disclosure.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking and parallel processing may be advantageous.

Moreover, the separation and/or integration of various system modules and components in the implementations described above should not be understood as requiring such separation and/or integration in all implementations, and it should be understood that the described program components and systems can generally be integrated together in a single software product or packaged into multiple software products.

Accordingly, the above description of example implementations does not define or constrain this disclosure. Other changes, substitutions, and alterations are also possible without departing from the spirit and scope of this disclosure.

What is claimed is:

1. A computer-implemented method comprising:
calibrating an observation unit (OU) sensor and an auxiliary observation unit (AOU) sensor in relation to an ambient environment;
calibrating the OU sensor and the AOU sensor in relation to an observational subject, wherein the OU sensor and the AOU sensor are located remotely from the observational subject;
establishing, using a receiving apparatus (RA) comprising at least one processor, monitoring parameters to be monitored from the calibrated sensors, wherein the monitoring parameters comprise a temperature threshold of the observational subject, a respiratory rate threshold of the observational subject, and a heart rate threshold of the observational subject;
gathering electromagnetic data by the calibrated OU sensor and the calibrated AOU sensor from electromagnetic radiation emitted by the observational subject, wherein the electromagnetic data comprises an infrared (IR) thermal image and a daylight image;
gathering heart rate data by the calibrated OU sensor and the calibrated AOU sensor;
determining a heart rate of the observational subject from the gathered heart rate data;
determining from the electromagnetic data, a temperature and a respiratory rate of the observational subject, and determining subject data comprising the temperature, the respiratory rate, and the heart rate of the observational subject;
merging the IR thermal image and the daylight image to form a low-light image;
providing the low-light image for display at the RA;
determining that the subject data exceeds the established monitoring parameters; and
generating one or more alerts based on determining that the subject data exceeds the established monitoring parameters,
wherein calibrating the OU sensor and the AOU sensor in relation to the ambient environment comprises calibrating at least one of the OU sensor and the AOU sensor thermally using the thermal image.

2. The computer-implemented method of claim 1, wherein calibrating the OU sensor and the AOU sensor in relation to the ambient environment comprises calibrating the OU sensor and the AOU sensor in relation to data related to at least one of audio, temperature, pressure, light level, humidity, or olfactory condition.

3. The computer-implemented method of claim 1, wherein calibrating the OU sensor and the AOU sensor in relation to the observational subject comprises calibrating the OU sensor and the AOU sensor in relation to at least one of a skin temperature, breath temperature, breath regularity, breath clarity, chest rise or fall, heart rate, heart regularity, or body position using position mapping.

4. The computer-implemented method of claim 1, wherein calibrating the OU sensor and the AOU sensor in relation to the ambient environment comprises calibrating at least one of the OU sensor and the AOU sensor thermally using an ambient environmental temperature.

5. The computer-implemented method of claim 1, comprising including metadata with the gathered electromagnetic data from the calibrated OU sensor or the calibrated AOU sensor.

6. The computer-implemented method of claim 5, wherein the metadata comprises at least one of time, date, geographic location, time span, security data, observer identification, or subject identification.

7. The computer-implemented method of claim 1, wherein the AOU sensor is placed on, in, or underneath a mattress.

8. A non-transitory, computer-readable medium storing one or more instructions executable by a computer system to perform operations comprising:
calibrating an observation unit (OU) sensor and an auxiliary observation unit (AOU) sensor in relation to an ambient environment;
calibrating the OU sensor and the AOU sensor in relation to an observational subject, wherein the OU sensor and the AOU sensor are located remotely from the observational subject;
establishing, using a receiving apparatus (RA) comprising at least one processor, monitoring parameters to be monitored from the calibrated sensors, wherein the monitoring parameters comprise a temperature threshold of the observational subject, a respiratory rate threshold of the observational subject, and a heart rate threshold of the observational subject;
gathering electromagnetic data by the calibrated OU sensor and the calibrated AOU sensor from electromagnetic radiation emitted by the observational subject, wherein the electromagnetic data comprises an infrared (IR) thermal image and a daylight image;
gathering heart rate data by the calibrated OU sensor and the calibrated AOU sensor;
determining a heart rate of the observational subject from the gathered heart rate data;
determining from the electromagnetic data, a temperature and a respiratory rate of the observational subject, and determining subject data comprising the temperature, the respiratory rate, and the heart rate of the observational subject;
merging the IR thermal image and the daylight image to form a low-light image;
providing the low-light image for display at the RA;
determining that the subject data exceeds the established monitoring parameters; and
generating one or more alerts based on determining that the subject data exceeds the established monitoring parameters,
wherein calibrating the OU sensor and the AOU sensor in relation to the ambient environment comprises calibrating at least one of the OU sensor and the AOU sensor thermally using the thermal image.

9. The non-transitory, computer-readable medium of claim 8, wherein calibrating the OU sensor and the AOU sensor in relation to the ambient environment comprises calibrating the OU sensor and the AOU sensor in relation to data related to at least one of audio, temperature, pressure, light level, humidity, or olfactory condition.

10. The non-transitory, computer-readable medium of claim 8, wherein calibrating the OU sensor and the AOU sensor in relation to the observational subject comprises calibrating the OU sensor and the AOU sensor in relation to at least one of a skin temperature, breath temperature, breath regularity, breath clarity, chest rise or fall, heart rate, heart regularity, or a body position using position mapping.

11. The non-transitory, computer-readable medium of claim 8, wherein calibrating the OU sensor and the AOU sensor in relation to the ambient environment comprises calibrating the OU sensor and the AOU sensor thermally using an ambient environmental temperature.

12. The non-transitory, computer-readable medium of claim 8, comprising instructions to include metadata with the gathered electromagnetic data from the calibrated OU sensor or the calibrated AOU sensor.

13. The non-transitory, computer-readable medium of claim 12, wherein the metadata comprises at least one of time, date, geographic location, time span, security data, observer identification, or subject identification.

14. The non-transitory, computer-readable medium of claim 8, wherein the AOU sensor is placed on, in, or underneath a mattress.

15. A computer system, comprising:
a computer memory; and
a hardware processor interoperably coupled with the computer memory and configured to perform one or more operations comprising:
calibrating an observation unit (OU) sensor and an auxiliary observation unit (AOU) sensor in relation to an ambient environment;
calibrating the OU sensor and the AOU sensor in relation to an observational subject, wherein the OU sensor and the AOU sensor are located remotely from the observational subject;
establishing, using a receiving apparatus (RA) comprising at least one processor, monitoring parameters to be monitored from the calibrated sensors, wherein the monitoring parameters comprise a temperature threshold of the observational subject, a respiratory rate threshold of the observational subject, and a heart rate threshold of the observational subject;
gathering electromagnetic data by the calibrated OU sensor and the calibrated AOU sensor from electromagnetic radiation emitted by the observational subject, wherein the electromagnetic data comprises an infrared (IR) thermal image and a daylight image;
gathering heart rate data by the calibrated OU sensor and the calibrated AOU sensor;
determining a heart rate of the observational subject from the gathered heart rate data;
determining from the electromagnetic data, a temperature and a respiratory rate of the observational subject, and determining subject data comprising the temperature, the respiratory rate, and the heart rate of the observational subject;
merging the IR thermal image and the daylight image to form a low-light image;
providing the low-light image for display at the RA;
determining that the subject data exceeds the established monitoring parameters; and
generating one or more alerts based on determining that the subject data exceeds the established monitoring parameters,
wherein calibrating the OU sensor and the AOU sensor in relation to the ambient environment comprises calibrating at least one of the OU sensor and the AOU sensor thermally using the thermal image.

16. The computer system of claim 15, wherein calibrating the OU sensor and the AOU sensor in relation to the ambient environment comprises calibrating the OU sensor and the AOU sensor in relation to data related to at least one of audio, temperature, pressure, light level, humidity, or olfactory condition.

17. The computer system of claim 15, wherein calibrating the OU sensor and the AOU sensor in relation to the observational subject comprises calibrating the OU sensor and the AOU sensor in relation to at least one of a skin temperature, breath temperature, breath regularity, breath clarity, chest rise or fall, heart rate, heart regularity, or a body position using position mapping.

18. The computer system of claim 15, configured to perform one or more operations comprising including metadata with the gathered electromagnetic data from the calibrated OU sensor or the calibrated AOU sensor.

19. The computer system of claim 18, wherein the metadata comprises at least one of time, date, geographic location, time span, security data, observer identification, or subject identification.

20. The computer system of claim 15, wherein the AOU sensor is placed on, in, or underneath a mattress.

* * * * *